United States Patent
Saatchi et al.

(10) Patent No.: US 9,931,489 B2
(45) Date of Patent: Apr. 3, 2018

(54) CROSS SLIT GASKET FOR INTRODUCER SHEATH

(71) Applicant: Medtronic Vascular, Inc., Santa Rosa, CA (US)

(72) Inventors: Sanaz Saatchi, San Francisco, CA (US); Andrew Murphy, Minneapolis, MN (US); Curtis Yarra, Minneapolis, MN (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 310 days.

(21) Appl. No.: 14/710,417

(22) Filed: May 12, 2015

(65) Prior Publication Data

US 2016/0331935 A1    Nov. 17, 2016

(51) Int. Cl.
*A61M 39/06* (2006.01)
*A61M 25/06* (2006.01)
(Continued)

(52) U.S. Cl.
CPC .... *A61M 25/0606* (2013.01); *A61M 25/0662* (2013.01); *A61M 39/06* (2013.01);
(Continued)

(58) Field of Classification Search
CPC .............. A61M 39/06; A61M 39/0606; A61M 39/0693; A61M 39/22; A61M 39/24;
(Continued)

(56) References Cited

U.S. PATENT DOCUMENTS

| 4,000,739 A | 1/1977 | Stevens |
| 4,424,833 A | 1/1984 | Spector et al. |

(Continued)

FOREIGN PATENT DOCUMENTS

| EP | 0399769 | 11/1990 |
| EP | 2213328 | 8/2010 |

(Continued)

OTHER PUBLICATIONS

PCT/US2016/032226, "The International Search Report and the Written Opinion of the International Searching Authority" dated Sep. 9, 2016.

*Primary Examiner* — Bhisma Mehta
*Assistant Examiner* — James D Ponton (57) ABSTRACT

A sheath introducer system including a sheath introducer defining a lumen therethrough and having a proximal valve housing in fluid communication with a distal tubular sheath, wherein a proximal end of the valve housing defines a proximal opening of the lumen of the sheath introducer. A gasket seated within the valve housing has a first surface, a second surface and an outer periphery extending between the first and second surfaces. A first slit is formed into the first surface having an inner surface defining a first gap. A second slit formed into the second surface having an inner surface defining a second gap. A notch extends into the first gap of the first slit forming a bump on the inner surface of the first slit, wherein the second slit intersects the first slit at the notch such that the notch prevents the first and second slits from being in fluid communication.

22 Claims, 8 Drawing Sheets

(51) Int. Cl.
*A61M 39/22* (2006.01)
*A61B 17/34* (2006.01)
*A61M 39/24* (2006.01)

(52) U.S. Cl.
CPC ......... *A61M 39/22* (2013.01); *A61B 17/3498* (2013.01); *A61M 2039/064* (2013.01); *A61M 2039/246* (2013.01); *A61M 2039/2426* (2013.01)

(58) Field of Classification Search
CPC ............ A61M 39/26; A61M 2039/062; A61M 2039/0626; A61M 2039/0633; A61M 2039/064; A61M 2039/066; A61M 2039/2426; A61M 2039/0646; A61M 2039/0653; A61B 17/3498
USPC ......... 604/87, 88, 167.02, 247, 288.02, 201, 604/202, 203, 204, 205, 206
See application file for complete search history.

(56) References Cited

U.S. PATENT DOCUMENTS

| | | |
|---|---|---|
| 4,610,665 A | 9/1986 | Matsumoto et al. |
| 4,798,594 A | 1/1989 | Hillstead |
| 5,006,113 A | 4/1991 | Fischer |
| 5,098,393 A | 3/1992 | Amplatz et al. |
| 5,125,903 A | 6/1992 | McLaughlin et al. |
| 5,304,156 A | 4/1994 | Sylvanowicz et al. |
| 6,352,520 B1 | 3/2002 | Miyazaki |
| 8,845,588 B2 | 9/2014 | Bruszewski |
| 2010/0185153 A1* | 7/2010 | Sugiki ............... A61M 39/0606 604/167.04 |
| 2014/0194833 A1 | 7/2014 | Andrus |

FOREIGN PATENT DOCUMENTS

| | | |
|---|---|---|
| WO | WO2004/032993 | 4/2004 |
| WO | WO2006/059540 | 6/2006 |

* cited by examiner

CROSS SLIT GASKET FOR INTRODUCER SHEATH

FIELD OF THE INVENTION

The invention relates to an introducer sheath assembly for enlarging and maintaining a percutaneous opening in an arterial or venous vessel for providing a pathway for the introduction of various sizes of interventional devices. More particularly, the invention is directed to an introducer sheath having a gasket ensuring hemostasis during introduction and manipulation of various medical devices.

BACKGROUND OF THE INVENTION

The introduction of interventional devices into a given arterial or venous blood vessel for a variety of purposes, such as for performing percutaneous transluminal coronary angioplasty (PTCA) or for delivering and implanting a stent or stent graft, is well known in the art. Several techniques for introducing such catheters are available, including the Seldinger technique. Broadly described the Seldinger technique involves surgically opening a vein or artery with a needle, inserting a guidewire into the vein or artery through the lumen of the needle, withdrawing the needle, inserting over the guidewire a dilator located inside an associated sheath introducer having a hemostasis valve, removing the dilator and guidewire, and inserting a catheter through the hemostasis valve and sheath into the blood vessel. During this process, care must be exercised to prevent introduction of air into the vessel and to avoid leakage of blood from a proximal end of the sheath introducer. To avoid the risk of both air embolism and blood contamination of the clinician, conventional introducers employ various types of hemostasis valves having a single proximal input port that is designed for use with catheters and guidewires that have various diameters.

In interventional procedures where it may be necessary to utilize different interventional devices, such as procedures for percutaneously delivering and implanting endovascular grafts for treatment of certain types of abdominal aortic aneurysms, a sheath introducer with a hemostasis valve having a single proximal input port may not ensure hemostasis of each interventional device in use during the procedure. In such cases, a clinician may utilize a puncturable hemostasis valve that can be adapted to achieve modest hemostasis of various devices to introduce additional device (s), although hemostasis is generally very poor with this practice. As such a need exists in the art for a sheath introducer that ensures hemostasis during treatments that require the introduction and manipulation of various catheters or other interventional devices.

Therefore, the prior art has addressed many configurations of hemostasis valves attempting to provide an adequate seal by a gasket at low and relatively higher blood pressure conditions for both air and blood while accommodating the wide range of diameters of devices inserted through the introducer sheath. Prior art hemostasis valves have, in many instances, been of the gasket sealing type, such as those shown in U.S. Pat. Nos. 4,000,739, 4,424,833, and 4,909, 798, which comprise a pin hole and a Y-shaped slit, back-to-back gasket assembly in either one or two-piece parts. The first, doughnut-shaped, gasket is provided with a hole slightly smaller than the diameter of the catheter to be inserted, while the second gasket is provided with a Y-shaped slit. When guide wires or catheters which are too small in diameter are inserted into this hemostasis valve, the sealing advantages of the first doughnut-shaped gasket are no longer available because the larger diameter doughnut hole will not seal around the smaller diameter guide wire or catheter. The two gaskets may be provided as separate back-to-back piece parts or as a single piece part, but in either case, are intended to reduce the possibility that blood would escape the hemostasis valve as the tip of the introduced instrument is withdrawn. Thus, the redundancy of the two seals is expected to reduce such leakage.

In still further attempts to accommodate various diameter therapeutic instruments and varying blood pressure between venous and arterial applications, introducers have employed hemostasis valves of the Tuohy-Borst type. For example, U.S. Pat. Nos. 4,726,374 and 4,723,550 provide at least one hemostasis valve assembled within a housing proximal to the side port, where the housing may be tightened down on the resilient gasket material of the valve to compress it to provide a variable pressure seal around the interventional device passing therethrough.

In yet another approach to providing a suitable seal under the varying conditions of usage encountered in practice, it has also been proposed in U.S. Pat. No. 4,917,668 to spring-load the resilient gasket valve member with one or more spring elements to augment the natural resilience of the gasket material.

The hemostasis valves described above all represent departures from and attempts to overcome deficiencies in flat-sided disk-shaped gaskets involving reduced diameter holes, slits and crossed slits therethrough to accommodate instruments passed through the valve housing and sheath, constituting an introducer sheath. It yet remains desirable to provide a simple, easy to manufacture hemostasis valve that is reliable in preventing leakage of blood or air and which possesses a feel of smoothness during insertion and withdrawal of all of the aforementioned varying diameter and material instruments therethrough.

BRIEF SUMMARY OF THE INVENTION

It is therefore an object of the present invention to provide a hemostasis valve, particularly in a device for enlarging and maintaining a percutaneous opening to a given arterial or venous vessel for the purpose of providing a pathway for the introduction of interventional devices.

It is a further object of the present invention to provide a simple, inexpensive, single piece molded gasket in a percutaneous catheter introducer.

It is a further object of the present invention to provide a gasket which is universally applicable for use in a given percutaneous catheter introducer to accommodate a variety of interventional devices having a range of diameters, without leakage of blood or air therethrough.

It is still another object of the present invention to construct a gasket for a percutaneous catheter introducer which will permit the introduction and passage of interventional devices therethrough, having a wide range of diameters while allowing the insertion and withdrawal of such devices without undue friction or pressure and thus providing the physician with the ability to feel the advancement of the device distally, through the chosen venous or arterial system.

BRIEF DESCRIPTION OF DRAWINGS

The foregoing and other features and advantages of the invention will be apparent from the following description of embodiments hereof as illustrated in the accompanying drawings.

The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to the treating clinician when describing an object or device manipulated by the clinician. "Distal" and "distally" are positions distant from or in a direction away from the clinician. "Proximal" and "proximally" are positions near or in a direction toward the clinician. The terms "distal" and "proximal", when used with respect to a position in a vessel refer to a position or direction relative to the direction of blood flow. Accordingly, "distal" and "distally" are positions downstream of a reference position, and "proximal" and "proximally" are positions upstream of the reference position.

The following detailed description is merely exemplary in nature and is not intended to limit the invention or the application and uses of the invention. Although the description of the invention is in the context of treatment of blood vessels such as the coronary arteries, the invention may also be used in any other body passageways where it is deemed useful such as but not limited to peripheral arteries, carotid arteries, renal arteries, and/or venous applications. Furthermore, there is no intention to be bound by any expressed or implied theory presented in the preceding technical field, background, brief summary or the following detailed description.

The improved hemostasis valve of the present invention is preferably incorporated in a PTCA introducer system. In PTCA, stenotic regions of coronary blood vessels are dilated by advancing a dilatation catheter through blood vessels into the stenotic region. The dilatation catheter advances over a guide wire, which itself is advanced in successive steps to the stenotic region. After placing the catheter in the desired position in the stenotic region, the guide wire may be removed. Alternatively, and particularly in fixed guide wire dilatation catheter PTCA devices, both the guide wire and the catheter are simultaneously advanced through a guide catheter which has been previously advanced through the outer sheath of the introducer.

Conventional introducers include the outer sheath extending distally from a valve housing. A side port in the valve housing distal to the valve itself is provided for the perfusion and aspiration of fluids through the sheath. The introducer sheath maintains the percutaneous opening or track initially made with other devices, such as a hypodermic needle or scalpel, and provides an entrance point for a dilator and obturator, as well as the aforementioned listed catheters and guide wires. The entrance point is located in the valve housing proximal to the hemostatic valve so that when the dilator, obturator, catheter or guide wire is introduced, it extends through the length of the sheath and out its distal opening, which is positioned in use a distance within the vein or artery accessed previously.

The introduction of the introducer sheath is accomplished, as mentioned above, by the dilator advancing over the indwelling guide wire, the dilator having been preloaded through the introducer sheath and valve. Once the introducer sheath is advanced a sufficient distance within the chosen vessel, the guide wire and dilator are removed in favor of the insertion of the therapeutic catheter system.

Figure 1:
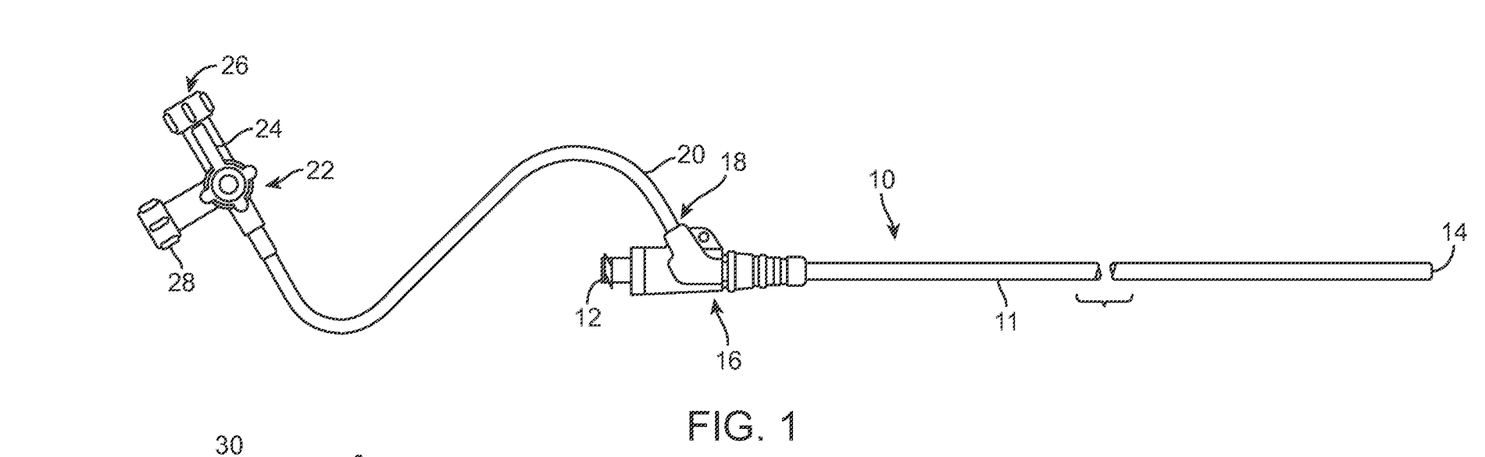
FIG. 1 is a side view of an introducer assembly in which the gasket of the present invention may be employed.
Figure 2:
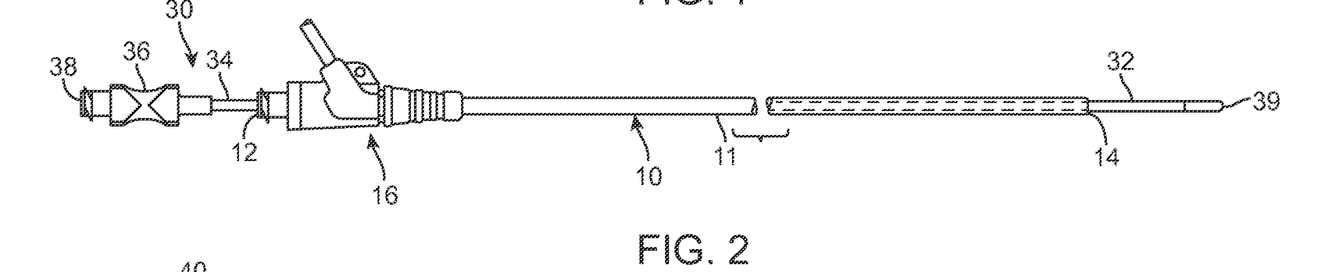
FIG. 2 is a side view of a dilator advanced partially into the introducer of FIG. 1.
Figure 3:
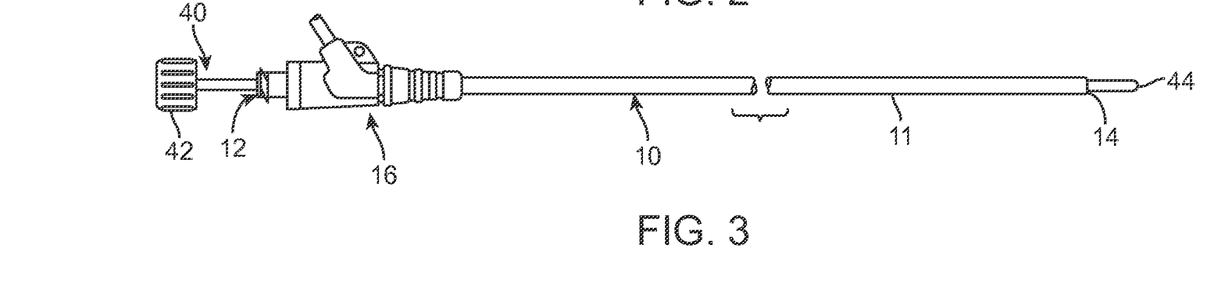
FIG. 3 is a side view of an obturator advanced partially into the introducer of FIG. 1.

FIGS. 1-3 illustrate in side views the PTCA catheter introducer 10 which has a proximal input port 12 for the introduction of the interventional devices described above and a distal opening 14 through which the interventional devices are advanced into the accessed vein or artery. Introducer 10 includes a valve assembly 16 having a side port 18 coupled by hose 20 to a stop cock assembly 22. In a well-known fashion, three-way stop cock assembly 22 permits continuous flushing or periodic aspiration and allows changes to be made from IV drip to emergency medications or pressure monitoring without disconnecting or reconnecting IV tubes. Generally, side port 18 is employed to facilitate perfusion and aspiration of fluids through the sheath 11.

The proximal opening 12 of the valve housing 16 is preferably fabricated having a connector or fitting that mate with the hubs of a dilator 30 and obturator 40 depicted in relation to the introducer 10 in FIGS. 2 and 3, respectively. Turning to FIG. 2, dilator 30 is depicted almost entirely advanced through the lumen of sheath 11 so that its distal end portion 32 extends out the distal opening 14. Attached to dilator proximal portion 34, a fitting 36 having a proximal port 38 is positioned to be advanced distally and compression fit into the fitting at proximal opening 12 of valve housing 16.

As explained above, dilator 30 is a hollow tubular device which enlarges the percutaneous opening initially made by other devices, such as hypodermic needles or scalpels, and it contains a single concentric lumen of sufficient diameter to allow for free movement of an appropriate sized guide wire therethrough. Thus, proximal opening 38 of dilator 30 provides access to interventional devices which are passed through the lumen of dilator 30 and out its distal portion 32 and distal opening 39 and thereafter into the accessed blood vessel. Distal portion 32 of dilator 30 can be tapered to provide a smooth transition over the guide wire advanced therethrough. Proximal opening 38 is created by a further fitting extending proximally from connector 36. The above-described introducer 10 and its associated dilator 30 and obturator 40 is conventional in the prior art in which the hemostasis valve of the present invention may be implemented.

Figure 4:
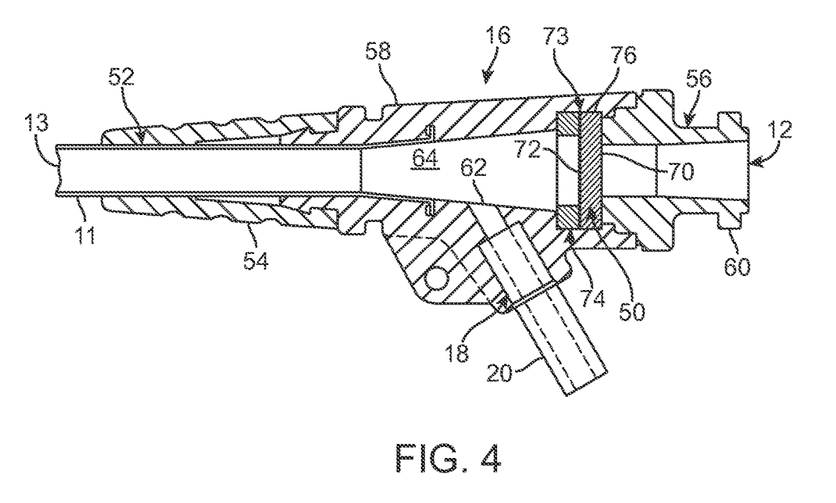
FIG. 4 is a longitudinal cross-sectional view of the valve housing of the introducer depicted in FIG. 1 showing the components thereof, including the gasket.

Turning now to FIG. 4, valve housing 16 is depicted in longitudinal cross-section in order to illustrate the location of a hemostasis valve gasket member 50 of the present invention. Valve housing 16 is coupled to the flexible, transparent tubing 20 at side port 18 and to the thin-walled, elongated sheath 11 which extends distally from a distal opening 52 of a housing body 58 as shown in FIGS. 1-3. A relatively soft elastomeric strain relief 54 surrounds a proximal section of the sheath 11 and a distal portion of valve housing 16 defining distal opening 52. Proximal connector fitting 56 is coupled to housing body 58 and provides opening 12 defined by connector 60. Side port 18 includes a bore 62 intersecting the inner chamber 64 of the elongated housing body 58 distal to the location of hemostasis valve gasket member 50. Thus, hemostasis valve housing 16, comprising the proximal fitting 56, elongated chamber 64 surrounded by body 58 and distal opening 52 and strain relief 54, defines an elongated chamber having proximal and distal ends and supports the hemostasis valve gasket member 50 therebetween. The gasket member 50 therefore normally seals chamber 64 from opening 12.

Hemostasis valve gasket 50 is generally disk-shaped having first and second opposite surfaces 70 and 72 and a cylindrical outer periphery 76. Gasket 50 is fitted into a cylindrical cavity 73 of body 58 having a distal annular seat 74 and retained there by longitudinal pressure exerted by body 58 generally or by pressure exerted against the peripheral portions of surfaces 70, 72 by the proximal fitting 56. In one example, ultrasonic welding is employed during assembly to attach the fitting 56 to proximal portion of body 58 compressing the peripheral portions of the surfaces 70, 72 and compressing the outer periphery 76 against seat 74. Gasket 50 also is provided with at least a pair of slits 80, 82 described hereinafter with reference to FIGS. 5-9 through which the distal ends of the dilator 30, obturator 40 or other interventional device may be advanced therethrough. Thus, as the interventional devices are introduced into opening 12, the devices pass through slits 80, 82, through chamber 64, through opening 52 and down through lumen 13 of tube 11 which is the portion of sheath 11 advanced into the blood vessel of interest.

Figure 5:
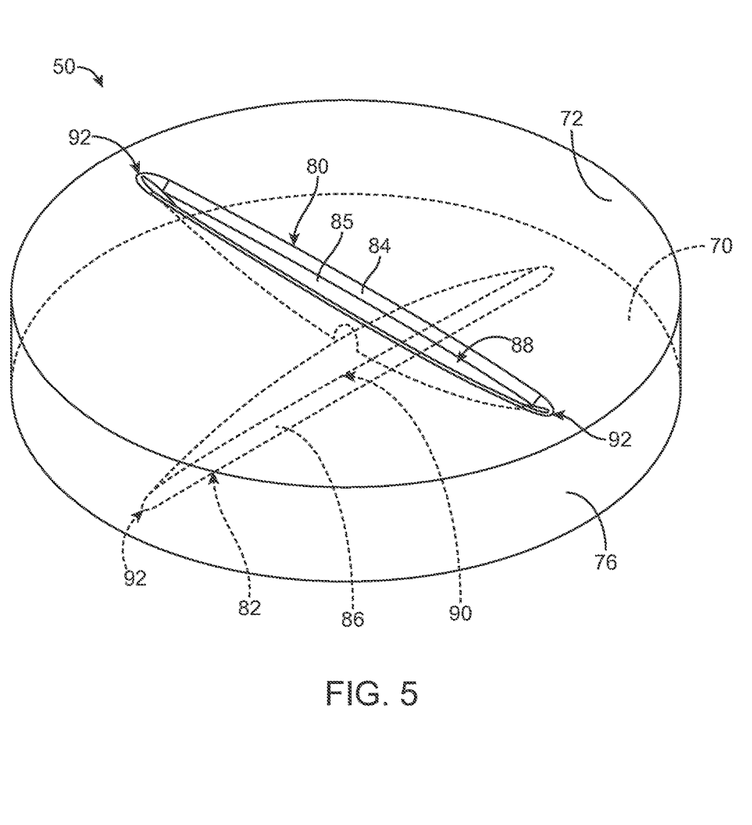
FIG. 5 is a perspective view of a gasket according to one example of the present invention.
Figure 6:
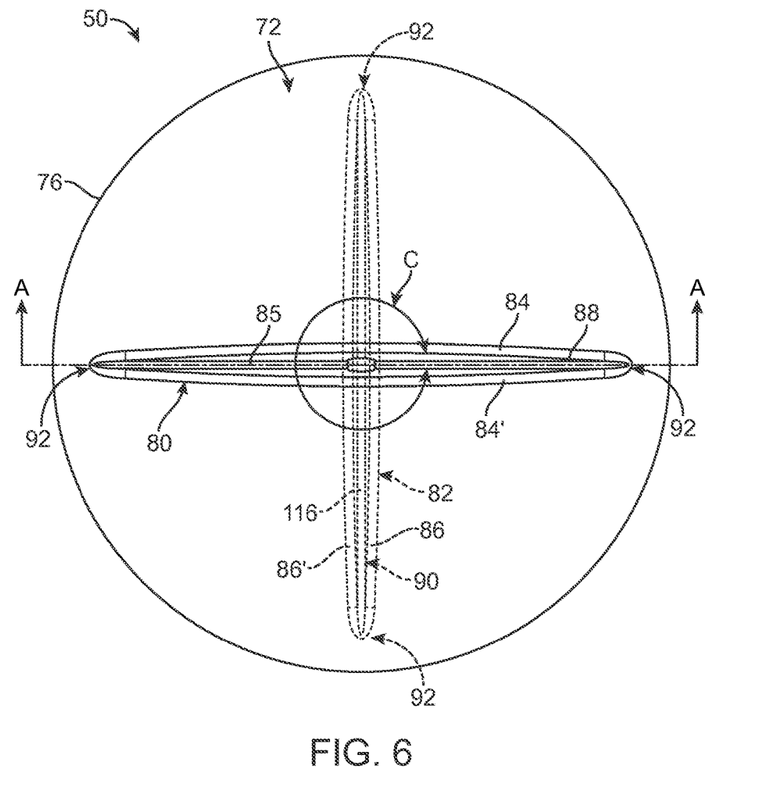
FIG. 6 is a top view of the gasket of FIG. 5 showing one slit in hidden lines.

FIG. 5 is a perspective view of hemostasis valve gasket member 50 with opposing slits formed into each surface 70, 72. FIG. 6 is a top view of gasket 50 with slit 80 in visible lines and slit 82 in hidden lines. Slits 80, 82 extend longitudinally across each surface 70, 72, respectively. In the as-molded, uncompressed configuration illustrated in FIGS. 5-9, gutter, channel or open slit 80 has opposing inner side surfaces 84, 84' and a bottom surface 85, which co-terminate at opposite ends 92. Inner side surfaces 84, 84' and bottom surface 85 define a gap 88. Similarly, groove, gutter, channel or open slit 82 has opposing inner side surfaces 86, 86' and a bottom surface 116, which co-terminate at opposite ends 92. Inner side surfaces 86, 86' and bottom surface 116 define a gap 90. Gaps 88, 90 extend along the length of each respective slit 80, 82. As shown in FIG. 6, both ends 92 of slits 80, 82 may be rounded. Although FIGS. 5-6 show slits 80, 82 orientated at 90 degrees to one another, slits 80, 82 could be orientated at different angles relative to one another. In one example of the present invention, the over-all diameter of the disk-shaped valve gasket member 50 is approximately 0.32 inches and its thickness is approximately 0.055 inches. Opposing surfaces 70, 72 are generally planar but in optional examples (not shown), surfaces 70, 72 could be concave or convex surfaces. In a preferred embodiment of the present invention, the lengths of slits 80, 82 are approximately 0.282 inches, but in optional examples, slits 80, 82 could be other lengths or the lengths of slits 80, 82 could be different from one another. Gasket 50 can be fabricated by transfer molding of polyisoprene from polyisoprene gum stock, silicone rubber, natural rubber or thermoplastic elastomers, e.g., injection moldable synthetic rubber compounds. The valve gasket 50 preferably has a Shore hardness of 40 A±5 A, although a hardness range of approximately 30 A to 50 A may be usable in practice.

Figure 7:
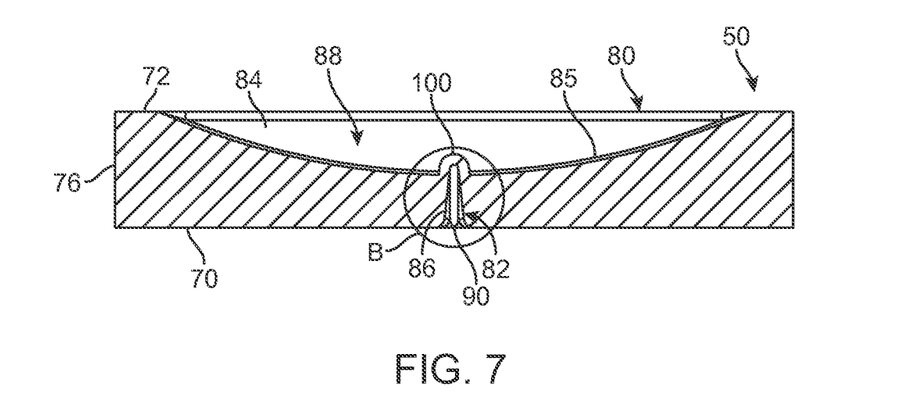
FIG. 7 is a cross-sectional view taken along lines A-A in FIG. 6.

FIG. 7 is a longitudinal cross-sectional view taken along line A-A of FIG. 6. In one example, bottom surface 85 of slit 80 defines an arcuate or concave shape formed into gasket 50 from first surface 70. Bottom surface 116 of slit 82 is similarly shaped, but in an inverted configuration with respect to bottom surface 85. In another example (not shown), bottom surface 85 of slit 80 could define a rectangular shape (or other alternative shapes) as opposed to an arcuate shape in the cross-sectional view of FIG. 7, and bottom surface 116 of slit 82 could be similarly shaped. At a region of intersection between slits 80, 82, a notch of gasket material 94 is formed between slits 80 and 82. The notch 94 extends into gap 88, thereby creating a protrusion or raised bump 100 on bottom surface 85 of slit 80. As shown in FIG. 7, slit 82 intersects slit 80 at notch 94 but because slits 80, 82 are separated by gasket material, bump 100 prevents slits 80, 82 from being in fluid communication with each other. Bump 100 is shown having an arcuate cross-sectional shape in FIG. 8. However, in other examples, bump 100 could have a rectangular, triangular or other cross-sectional shape.

Although FIG. 7 shows notch 94 and corresponding bump 100 disposed between slits 80, 82, in another embodiment, slits 80, 82 can be formed without notch 94 and bump 100, thereby having minimal or no intersection of slits 80, 82. In the case of minimal intersection, slits 80, 82 are formed so that either a thin layer of gasket material separates slits 80, 82; or slits 80, 82 intersect with another such that slits 80, 82 are in fluid communication.

Figure 8:
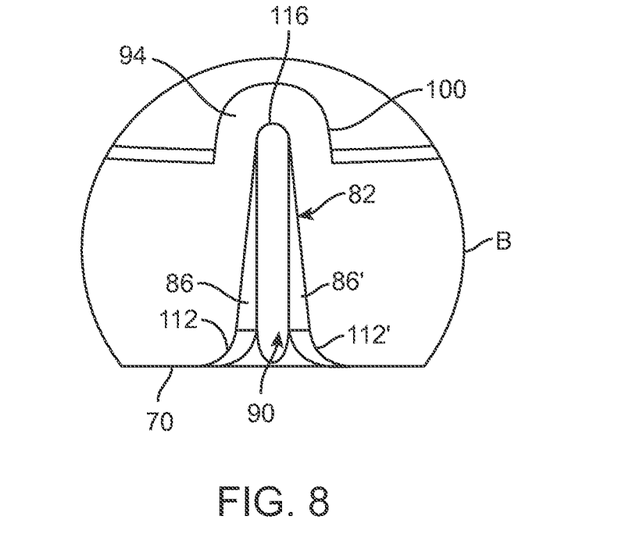
FIG. 8 is an enlarged view of region B in FIG. 7.

FIG. 8 is a close-up view of slit 82 taken from region B of FIG. 7. Opposing inner side surfaces 86, 86' extend from surface 70 to rounded or arcuate slit bottom 116. In the illustrated example, inner side surfaces 86, 86' are not parallel to each other such that slit 82 is narrower at bottom 116 than it is at surface 70. In another embodiment, inner side surfaces 86, 86' are not parallel to each other but slit 82 is wider at bottom 116 than it is at surface 70. In another embodiment, inner side surfaces 86, 86' could be substantially parallel and slit could be wider at bottom 116 than it is at surface 70 or slit could be narrower at bottom 116 than it is at surface 70. In addition, bottom 116 can have a variety of different geometries such as rectangular or triangular instead of the arcuate cross-sectional shape. As illustrated in most of the figures, and especially in the perspective view of FIG. 5, slit 82 is also narrower at the ends than it is in the middle where section line A-A crosses. Edges 112, 112' where side surfaces 86, 86' meet surface 70 may be chamfered or rounded, as shown. Thus, as illustrated, slit 82 defines gap 90 and slit 80 has a similar shape as slit 82, thereby defining gap 88.

Figure 9:
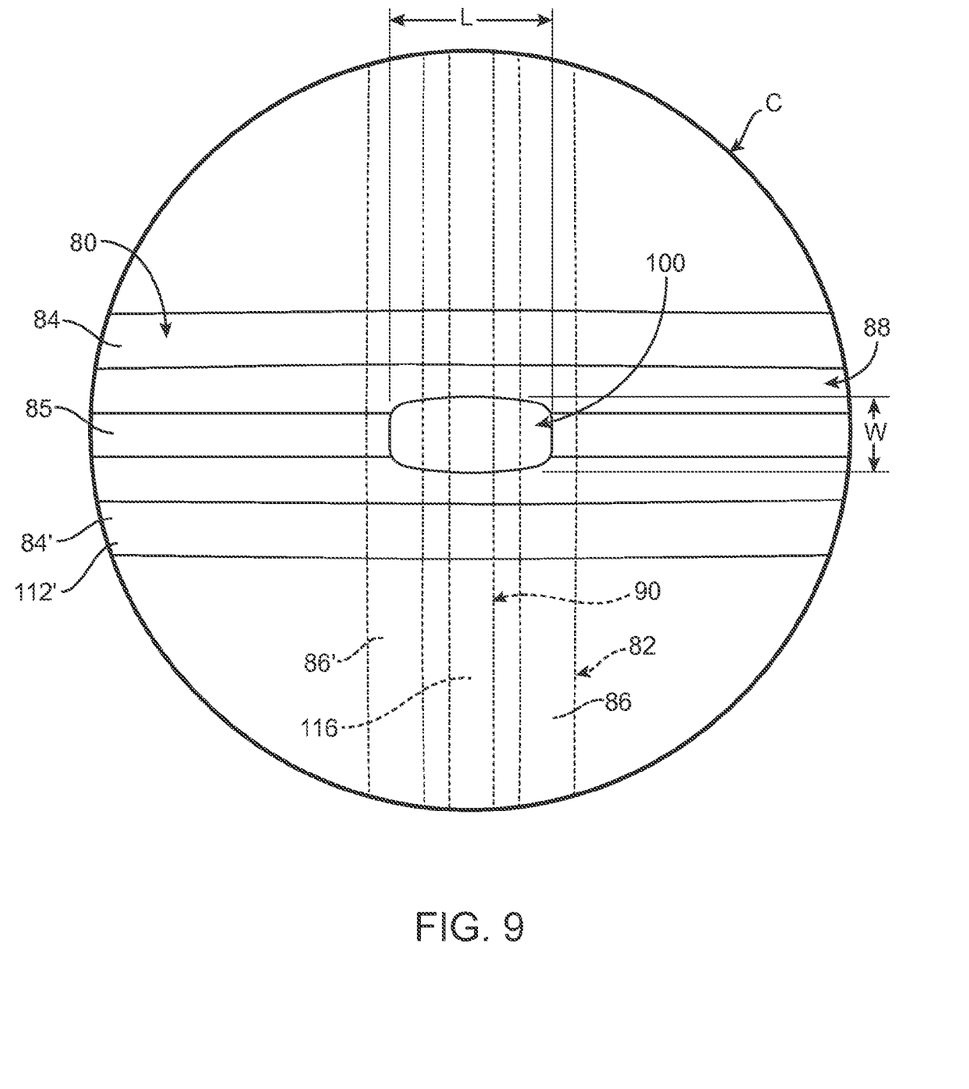
FIG. 9 is an enlarged view of region C in FIG. 6.

FIG. 9 is a close-up top view of region C of FIG. 6. As described above, slit 80 is shown in visible lines, while slit 82 is shown in hidden lines. FIG. 9 shows the top view of bump 100 formed on bottom surface 85 of slit 80. From a top view, bump 100 has a first dimension or length L which measures the distance bump 100 extends along the longitudinal length of slit 80. Bump 100 has a second dimension or width W which measures the distance bump 100 extends along the width of slit 80. Alternatively, W is the distance of the region of intersection between slits 80 and 82. Both first and second dimensions L, W are sized to provide enough gasket material to space apart slits 80, 82 at the intersection region. However, the sizes of first and second dimensions L, W can vary so long as the amount of gasket material separating spaced apart slits 80, 82 is enough to prevent fluid communication between slits 80, 82. Specifically, that first dimension L is large enough to prevent slit 82 from intersecting with slit 80 and causing fluid communication between gaps 88, 90. In addition, second dimension W needs to be large enough to prevent slit 82 from intersecting with slit 80 and causing fluid communication between gaps 88, 90.

Figure 10:
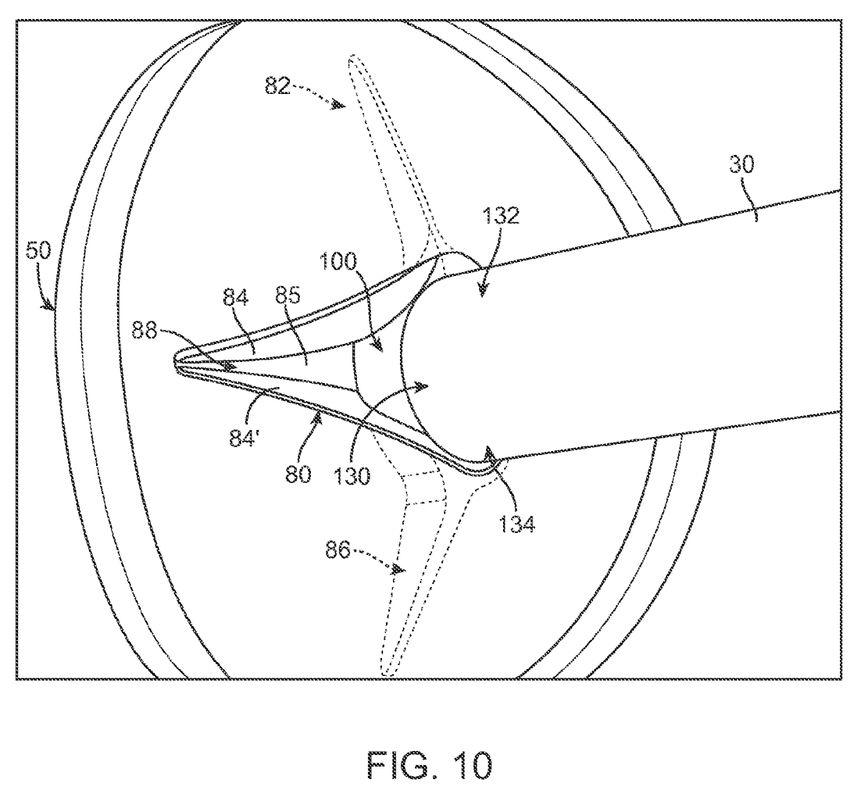
FIG. 10 is a perspective view of a dilator advanced through an opening of the gasket of FIG. 5

In order to advance dilator 30 or other interventional device through gasket 50 as described above, dilator 30 must first pass through slit 82 and bump 100 to then pass through slit 80. In one example, gasket 50 is lubricated and bump 100 is pre-pierced while gasket 50 is disposed within seat 74 of body 58. The pre-piercing of notch 100 would make it easier for the operator to pass dilator 30 (or other devices) through slit 82, notch 100 and slit 80. However, pre-lubrication and pre-piercing of bump 100 is not required and an operator could still pierce bump 100 during a procedure. FIG. 10 shows dilator 30 advanced through slits 80, 82 and bump 100. Due to the arrangement of slits 80, 82 and the gasket material or webbing, the opposing side surfaces 86, 86' of slit 82 and pierced bump 100 apply radial pressure to a first portion 130 and a second portion of dilator 30 (second portion is not shown in FIG. 10 and is on the opposite side of dilator 30 from first portion 130). The opposing side surfaces 84, 84' of slit 80 also apply radial pressure to a third portion 132 and a fourth portion 134 of dilator 30. The result is that dilator 30 has radial pressure substantially applied to the entire circumference of dilator 30 from slits 80, 82 thereby preventing the leakage of air or blood in introducer sheath.

Although slits 80, 82 can be formed into each surface 70, 72 by a variety of known techniques, such as cutting, in a preferred example of the present invention, slits 80, 82, the notch 94, and bump 100 are formed by molding gasket 50. Not only is molding slits 80, 82 into gasket 50 a more cost effective and less time consuming process than cutting, but also the molding process results in the walls of slits 80, 82 being initially spaced apart in a uncompressed configuration. In accordance with the invention, slits 80, 82 are molded as normally-open grooves wherein respective side surfaces 84, 84' and 86, 86' are spaced apart. During assembly, gasket 50 is fitted into cylindrical cavity 73 such that surface 72 abuts seat 74 of valve body 58. Fitting 56 is mounted in the proximal end of valve body 58 and applies longitudinal force to the gasket surface 70 thereby deforming at least one of the opposing side surfaces 84, 84' and 86, 86' of respective slits 80, 82 into abutment, thus closing at least one of gaps 88, 90. In an alternative embodiment, radial compression from valve assembly 16 applies a radial force against gasket 50 compressing the outer periphery 76, thereby deforming at least one of the opposing side surfaces 84, 84' and 86, 86' of respective slits 80, 82 into abutment, thus closing at least one of gaps 88, 90. Gasket 50 with slits 80, 82 formed as described herein has been found to provide an improved combination of adequate sealing and reduced friction in comparison to known slits which are simply cut into a gasket, as cut slits are already in closed to form a seal in an uncompressed configuration. When additional compression force from a valve housing (or other external source) is applied to cut slits, the additional pressure only further compresses what is already closed and sealed, and such additional pressure appears to increase sliding friction.

Figure 11A:
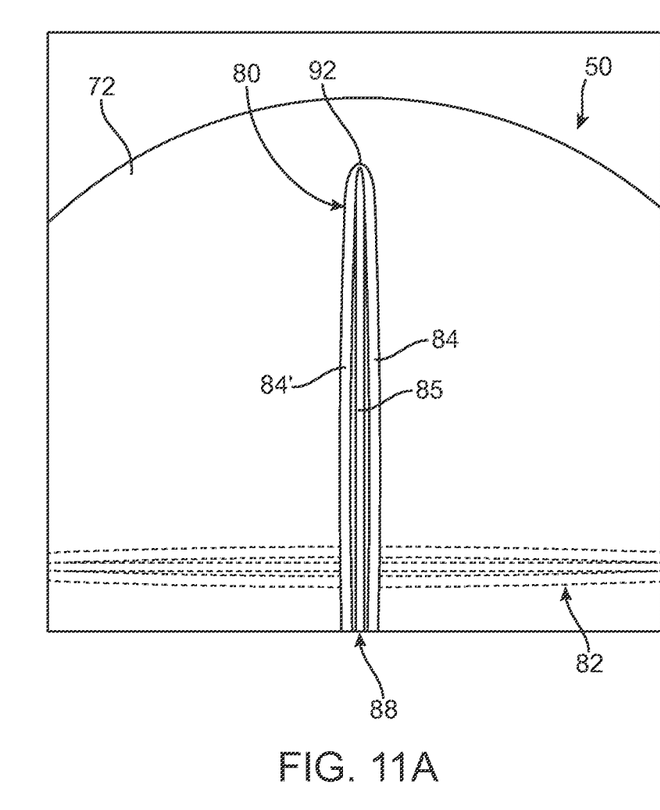
FIG. 11A is a top view of the gasket of FIG. 5 showing a portion of a slit in an as-molded, uncompressed configuration.
Figure 11B:
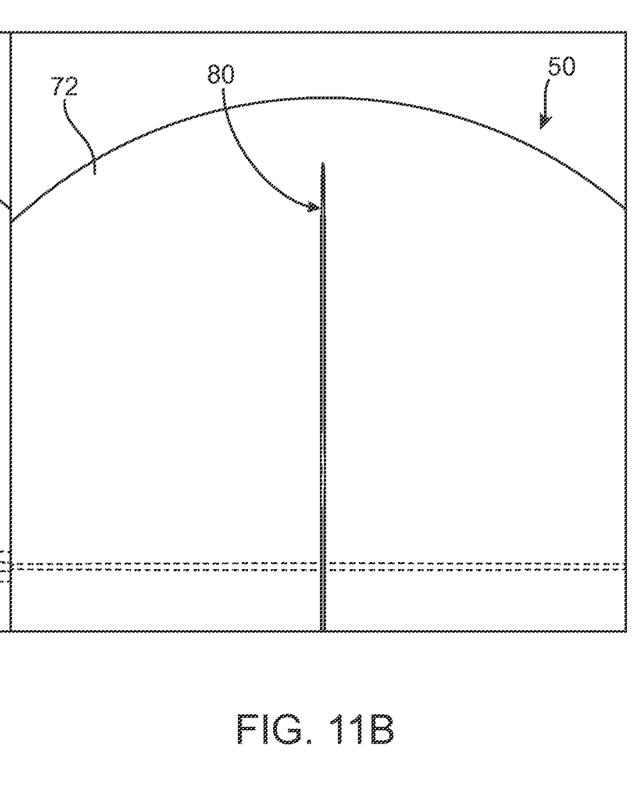
FIG. 11B is a top view of the same portion of the slit shown in FIG. 11A but in a compressed configuration, as assembled in the valve housing of FIG. 4.

FIG. 11A shows the initial molded gap 88 of slit 80 with no compression force exerted on gasket 50. FIG. 11B shows gasket 50 under compression force from fitting 56 resulting in the side surfaces of slit 80 coming together, eliminating gap 88.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment.

What is claimed is:

1. A gasket for a percutaneous catheter introducer comprising:
    a first surface, a second surface and an outer periphery extending between the first and second surfaces;
    a first slit formed into the first surface having an inner surface defining a first gap;
    a second slit formed into the second surface having an inner surface defining a second gap; and
    a notch extending into the first gap of the first slit forming a bump on the inner surface of the first slit, wherein the second slit intersects the first slit at the notch such that the notch prevents the first and second slits from being in fluid communication.

2. The gasket of claim 1, wherein at least one of the first and second gaps is open in an uncompressed configuration.

3. The gasket of claim 1 wherein the inner surface of the first slit has spaced apart opposing walls.

4. The gasket of claim 3, wherein the spaced apart walls converge at a rounded surface, the rounded surface extending along a longitudinal length of the first slit.

5. The gasket of claim 1, wherein the notch has a first dimension extending along a length of the first slit, and wherein the notch has a second dimension which has a maximum width substantially equal to a width of the first slit.

6. The gasket of claim 5, wherein the first dimension of the notch has sufficient length to prevent the second slit from establishing fluid communication between the first and second gaps of the first and second slits.

7. The gasket of claim 5, wherein the second dimension of the notch has sufficient width to prevent the second slit from establishing fluid communication between the first and second gaps of the first and second slits.

8. A sheath introducer system comprising:
    a sheath introducer defining a lumen therethrough and having a proximal valve housing in fluid communication with a distal tubular sheath, wherein a proximal end of the valve housing defines a proximal opening of the lumen of the sheath introducer; and
    a gasket seated within the valve housing, the gasket further comprising:

a first surface, a second surface and an outer periphery extending between the first and second surfaces;

a first slit formed into the first surface having an inner surface defining a first gap;

a second slit formed into the second surface having an inner surface defining a second gap; and a notch extending into the first gap of the first slit forming a bump on the inner surface of the first slit, wherein the second slit intersects the first slit at the notch such that the notch prevents the first and second slits from being in fluid communication.

9. The sheath introducer system of claim 8, wherein when the gasket is in a compressed configuration within the valve housing, at least one of the first and second gaps are closed forming a seal.

10. The sheath introducer system of claim 8, wherein the inner surface of the first slit has spaced apart opposing walls.

11. The sheath introducer system of claim 10, wherein the spaced apart walls converge at a rounded surface, the rounded surface extending along a longitudinal length of the first slit.

12. The sheath introducer system of claim 8, wherein the notch has a first dimension extending along a length of the first slit, and wherein the notch has a second dimension which has a maximum width substantially equal to a width of the first slit.

13. The sheath introducer system of claim 12, wherein the first dimension of the notch has sufficient length to prevent the second slit from establishing fluid communication between the first and second gaps of the first and second slits.

14. The sheath introducer system of claim 12, wherein the second dimension of the notch has sufficient width to prevent the second slit from establishing fluid communication between the first and second gaps of the first and second slits.

15. A gasket for a percutaneous catheter introducer, the gasket being formed from a gasket material, the gasket comprising:

a first surface, a second surface and an outer periphery extending between the first surface and the second surface;

a first slit formed into the first surface having an inner surface defining a first gap;

a second slit formed into the second surface having an inner surface defining a second gap; and a notch of the gasket material extending into the first gap of the first slit, the notch thereby creating a raised bump on the inner surface of the first slit, wherein the second slit intersects the first slit at the notch and the notch prevents the first slit and the second slit from being in fluid communication.

16. The gasket of claim 15, wherein at least one of the first gap and the second gap is open in an uncompressed configuration.

17. The gasket of claim 15, wherein the inner surface of the first slit has spaced apart walls that oppose each other.

18. The gasket of claim 17, wherein the spaced apart walls converge at a rounded surface, the rounded surface extending along a longitudinal length of the first slit.

19. The gasket of claim 15, wherein the notch has a first dimension extending along a length of the first slit, and wherein the notch has a second dimension which has a maximum width substantially equal to a width of the first slit.

20. The gasket of claim 19, wherein the first dimension of the notch has sufficient length to prevent the second slit from establishing fluid communication between the first gap and the second gap of the first slit and the second slit, respectively.

21. The gasket of claim 19, wherein the second dimension of the notch has sufficient width to prevent the second slit from establishing fluid communication between the first gap and the second gap of the first slit and the second slit, respectively.

22. The gasket of claim 15, wherein the raised bump has an arcuate cross-sectional shape.

* * * * *